(12) United States Patent
Nakamura

(10) Patent No.: US 10,515,745 B2
(45) Date of Patent: Dec. 24, 2019

(54) MEDICAL COAXIAL CONNECTOR, MEDICAL COAXIAL CABLE, AND MEDICAL OBSERVATION SYSTEM

(71) Applicant: Sony Olympus Medical Solutions Inc., Tokyo (JP)

(72) Inventor: Yasuma Nakamura, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 15/810,195

(22) Filed: Nov. 13, 2017

(65) Prior Publication Data
US 2018/0158576 A1    Jun. 7, 2018

(30) Foreign Application Priority Data

Dec. 6, 2016 (JP) ................................ 2016-236832

(51) Int. Cl.
| | |
|---|---|
| *H01R 9/05* | (2006.01) |
| *H01B 11/18* | (2006.01) |
| *A61B 1/04* | (2006.01) |
| *H01R 24/40* | (2011.01) |
| *A61B 1/00* | (2006.01) |
| *H01R 12/59* | (2011.01) |
| *H01R 103/00* | (2006.01) |

(52) U.S. Cl.
CPC ...... *H01B 11/1843* (2013.01); *A61B 1/00124* (2013.01); *A61B 1/041* (2013.01); *H01B 11/1808* (2013.01); *H01R 24/40* (2013.01); *A61B 1/00018* (2013.01); *H01B 11/1847* (2013.01); *H01B 11/1895* (2013.01); *H01R 12/594* (2013.01); *H01R 2103/00* (2013.01); *H01R 2201/12* (2013.01)

(58) Field of Classification Search
CPC ...................................................... H01R 9/0503
USPC ................................. 174/88 C; 439/578, 585
See application file for complete search history.

(56) References Cited

U.S. PATENT DOCUMENTS

| | | | | | |
|---|---|---|---|---|---|
| 2,966,645 | A | * | 12/1960 | Bird ........................ | H01R 24/44 174/88 C |
| 3,331,917 | A | * | 7/1967 | O'Keefe .............. | H01R 9/0503 174/75 C |

(Continued)

FOREIGN PATENT DOCUMENTS

JP    2000-316795    11/2000

*Primary Examiner* — Chau N Nguyen
(74) *Attorney, Agent, or Firm* — Xsensus LLP

(57) ABSTRACT

A medical coaxial connector includes: an internal conductor configured to be electrically connected to an other-side inner conductor when the medical coaxial connector is connected to an other-side medical coaxial connector; an outer conductor electrically connected to the inner conductor, formed in a tubular shape surrounding the inner conductor, and configured to be electrically connected to an other-side outer conductor when the medical coaxial connector is connected to the other-side medical coaxial connector; and an insulating body that is placed on inner periphery side of the outer conductor and formed in a cylindrical shape surrounding the inner conductor. The insulating body is configured to be placed on inner periphery side of the other-side outer conductor and a leading end of the insulating body in a connection direction toward the other-side coaxial connector is configured to protrude more in the connection direction than the inner conductor.

20 Claims, 14 Drawing Sheets

(56) References Cited

U.S. PATENT DOCUMENTS

| | | | | |
|---|---|---|---|---|
| 3,871,735 A | * | 3/1975 | Herrmann, Jr. | H01R 13/53 439/281 |
| 4,377,320 A | * | 3/1983 | Lathrop | H01R 24/40 439/585 |
| 4,412,717 A | * | 11/1983 | Monroe | H01R 9/0518 439/581 |
| 5,232,377 A | * | 8/1993 | Leibfried, Jr. | H01R 4/024 439/320 |
| 5,274,917 A | * | 1/1994 | Corbett, III | H01R 13/22 264/263 |
| 7,361,837 B2 | * | 4/2008 | Wells | H01R 9/031 174/74 R |
| 8,961,224 B2 | * | 2/2015 | Grek, IV | H01R 9/0503 439/578 |

* cited by examiner

MEDICAL COAXIAL CONNECTOR, MEDICAL COAXIAL CABLE, AND MEDICAL OBSERVATION SYSTEM

CROSS-REFERENCE TO RELATED APPLICATION(S)

The present application claims priority to and incorporates by reference the entire contents of Japanese Patent Application No. 2016-236832 filed in Japan on Dec. 6, 2016.

BACKGROUND

The present disclosure relates to a medical coaxial connector, a medical coaxial cable, and a medical observation system.

Typically, in the medical field, a medical observation system is known that includes a medical signal processing device for outputting video signals according to the examination results of the inside of the subject being examined such as a person (of the inside of the body) and a display device for displaying images based on the video signals; and that is used in observing the inside of the body. In a medical observation system in which high-definition video signals of the 4K resolution (hereinafter, written as 4K) are processed and in which real-time processing is necessary, a BNC-type medical coaxial connector of the SDI standard (SDI stands for Serial Digital Interface) and having less delay is used for transmitting the video signals between the medical signal processing device and the display device (for example, see Japanese Laid-open Patent Publication No. 2000-316795).

SUMMARY

FIGS. 13 to 15 are diagrams for explaining the issues faced in a medical observation system 100. More particularly, FIG. 13 schematically illustrates a medical signal processing device 900; a display device 700; and a medical coaxial cable 800, which connects the medical signal processing device 900 with the display device 700 and which transmits video signals from the medical signal processing device 900 to the display device 700. Moreover, with reference to FIG. 13, BNC-type medical coaxial connectors 1300 are installed at both ends of the medical coaxial cable 800. Furthermore, with reference to FIG. 13, an other-side medical coaxial connector 1100 is installed in the medical signal processing device 900 as well as in the display device 700, and is connected to one of the medical coaxial connectors 1300. Moreover, with reference to FIG. 13, a transmitter 901 is installed in the medical signal processing device 900 for transmitting video signals to the display device 700 via the medical coaxial cable 800. Furthermore, with reference to FIG. 13, a receiver 701 is installed in the display device 700 for receiving the video signals transmitted from the medical signal processing device 900 via the medical coaxial cable 800. FIG. 14 is a diagram illustrating a state in which the medical coaxial connector 1300 is connected to the other-side medical coaxial connector 1100. FIG. 15 is an enlarged cross-sectional view of FIG. 14.

As illustrated in FIGS. 14 and 15, the medical coaxial connector 1300 includes an inner conductor 1310 and a tubular outer conductor 1350 that is electrically insulated from the inner conductor 1310 and that surrounds the inner conductor 1310. In an identical manner, each other-side medical coaxial connector 1100 includes an other-side inner conductor 1110 (FIG. 15) and a tubular other-side outer conductor 1130 that is electrically insulated from the other-side inner conductor 1110 and that surrounds the other-side inner conductor 1110.

The leading end of the inner conductor 1310 is positioned slightly deeper than the leading end of the outer conductor 1350. For that reason, usually it is less likely that a finger touches the inner conductor 1310 thereby resulting in electrostatic discharge between that finger and the inner conductor 1310. However, as illustrated in FIGS. 14 and 15, if the medical coaxial connector 1300 is pressed at a slant against the other-side medical coaxial connector 1100, then the other-side outer conductor 1130 may make contact with the inner conductor 1310 thereby resulting in electrostatic discharge between the other-side outer conductor 1130 and the inner conductor 1310.

In the state in which the medical coaxial cable 800 (one of the medical coaxial connectors 1300) is connected to the medical signal processing device 900 (the other-side medical coaxial connector 1100), assume that the remaining medical coaxial connector 1300 is pressed at a slant against the display device 700 (the other-side medical coaxial connector 1100) (FIG. 13).

In that case, the electrically-charged other-side outer conductor 1130 on the side of the display device 700 makes contact with the inner conductor 1310 having the same electrical potential as the electrical potential of the circuit (such as the transmitter 901) inside the medical signal processing device 900 of the other medical coaxial connector 1300, thereby resulting in electrostatic discharge between the other-side outer conductor 1130 and the inner conductor 1310. Because of that, there is a risk of damaging the circuit (such as the transmitter 901) inside the medical signal processing device 900.

In order to solve that issue, it is possible to think of installing an electrostatic discharge (ESD) protection device such as a diode or a varistor in the signal line leading from the inner conductor 1310 up to the concerned circuit (such as the transmitter 901). However, if an ESD protection device is installed, the video signals become weaker. Particularly, in the case of processing high-definition video signals of the 4K resolution, it is not desirable to install an ESD protection device.

In that regard, there is a demand for a technology that, at the time of connecting the medical coaxial connector 1300 to the other-side medical coaxial connector 1100, enables avoiding contact of the other-side outer conductor 1130 with the inner conductor 1310.

The present disclosure has been made in view of the issues mentioned above, and it is an object of the present disclosure to provide a medical coaxial connector, a medical coaxial cable, and a medical observation system that, at the time of establishing connection with the other-side medical coaxial connector, enable avoiding contact of the other-side outer conductor with the inner conductor.

According to one aspect of the present disclosure, there is provided a medical coaxial connector of a Bayonet Neill Concelman type adapted to be connected to an other-side medical coaxial connector, and transmit to the other-side medical coaxial connector a video signal according to examination results of a subject, the other-side medical coaxial connector including an other-side inner conductor, and an other-side outer conductor electrically connected to the other-side inner conductor and formed in a tubular shape surrounding the other-side inner conductor, the medical coaxial connector including: an internal conductor configured to be electrically connected to the other-side inner conductor when the medical coaxial connector is connected to the other-side medical coaxial connector; an outer conductor electrically connected to the inner conductor, formed in a tubular shape surrounding the inner conductor, and configured to be electrically connected to the other-side outer conductor when the medical coaxial connector is connected to the other-side medical coaxial connector; and an insulating body that is placed on inner periphery side of the outer conductor and formed in a cylindrical shape surrounding the inner conductor, wherein the insulating body is configured to be placed on inner periphery side of the other-side outer conductor and a leading end of the insulating body in a connection direction toward the other-side coaxial connector is configured to protrude more in the connection direction than the inner conductor when the medical coaxial connector is connected to the other-side medical coaxial connector.

DETAILED DESCRIPTION

Figure 1:
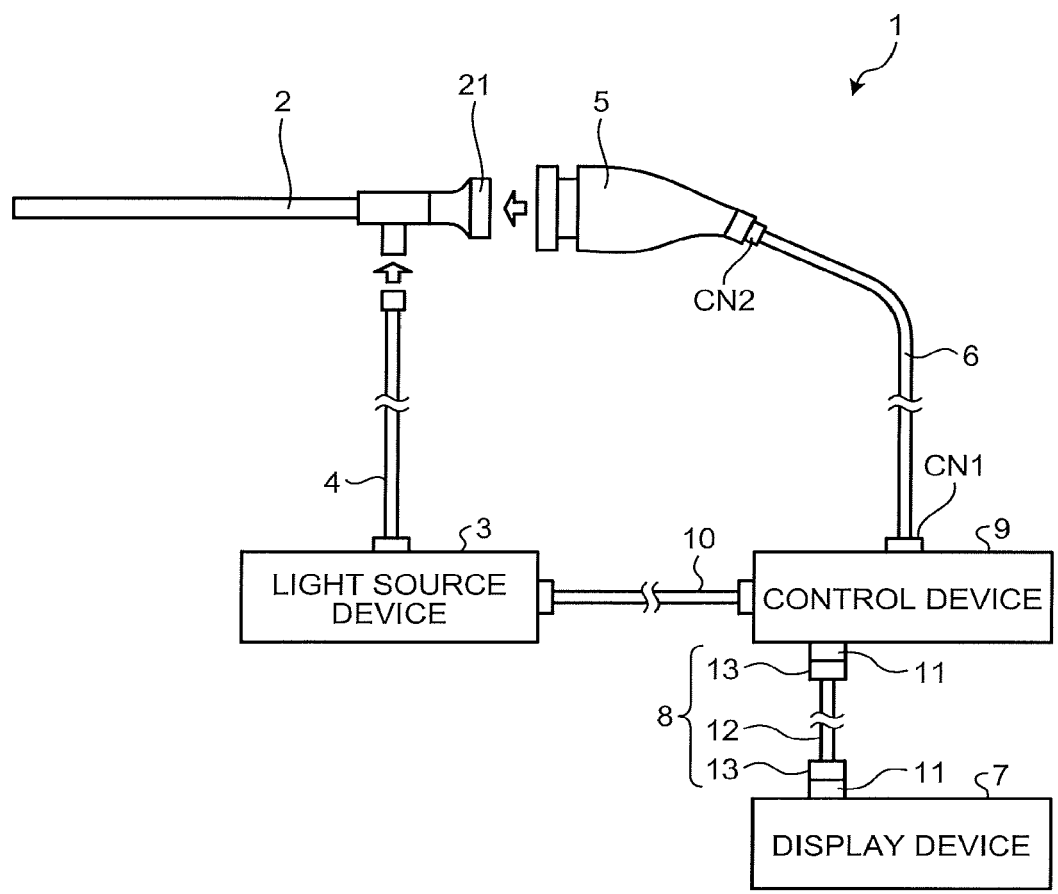
FIG. 1 is a diagram illustrating an overall configuration of a medical observation system according to a first embodiment.

Preferred embodiments are described below with reference to the accompanying drawings. However, the present disclosure is not limited by the embodiments described below. Moreover, in the drawings, the same constituent elements are referred to by the same reference numerals.

First Embodiment

Overall configuration of medical observation system FIG. 1 is a diagram illustrating an overall configuration of a medical observation system 1 according to a first embodiment.

The medical observation system 1 is used in the medical field for observing the subject being examined such as the inside of a body. As illustrated in FIG. 1, the medical observation system 1 includes an inserting unit 2, a light source device 3, a light guide 4, a camera head 5, a first transmission cable 6, a display device 7, a second transmission cable 8, a control device 9, and a third transmission cable 10.

In the first embodiment, the inserting unit 2 is configured with a rigid endoscope. That is, the inserting unit 2 has an elongate shape made of a rigid material or at least partially made of a soft material, and is inserted inside the body. Inside the inserting unit 2, an optical system is installed that is configured with one or more lenses and that collects the light coming from subject images.

The light source device 3 has one end of the light guide 4 connected thereto and, under the control of the control device 9, supplies light to that one end of the light guide 4 for illuminating the inside of the body.

The light guide 4 has one end thereof connected to the light source device 3 in a detachably attachable manner, and has the other end thereof connected to the inserting unit 2 in a detachably attachable manner. The light guide 4 transmits the light, which is supplied from the light source device 3, from one end to the other end thereof and supplies the light to the inserting unit 2. The light supplied to the inserting unit 2 then exits from the leading end of the inserting unit 2, and thus the inside of the body gets illuminated. The light (the subject image) illuminating the inside of the body is then collected by the optical system installed in the inserting unit 2.

The camera head 5 is connected to the base end (an eyepiece portion 21 (FIG. 1)) of the inserting unit 2 in a detachably attachable manner. Then, under the control of the control device 9, the camera head 5 performs imaging of the subject image that has been focused in the inserting unit 2 and outputs image signals (RAW signals) resulting from the imaging. In the first embodiment, the image signals have the resolution of 4K resolution or beyond.

The first transmission cable 6 has one end thereof connected to the control device 9 via a connector CN1 (FIG. 1) in a detachably attachable manner, and has the other end thereof connected to the camera head 5 via a connector CN2 (FIG. 1) in a detachably attachable manner. The first transmission cable 6 transmits the image signals, which are output from the camera head 5, to the control device 9; as well as transmits control signals, synchronization signals, a clock, and electrical power, which are output from the control device 9, to the camera head 5.

Regarding the transmission of image signals from the camera head 5 to the control device 9 via the first transmission cable 6, the image signals may be transmitted either as light signals or as electrical signals. The same is the case about the transmission of control signals, synchronization signals, and the clock from the control device 9 to the camera head 5 via the first transmission cable 6.

The display device 7 is configured using a display such as a liquid crystal display or an organic electroluminescence (EL) display, and is used to display images based on the video signals processed by the control device 9.

Figure 2:
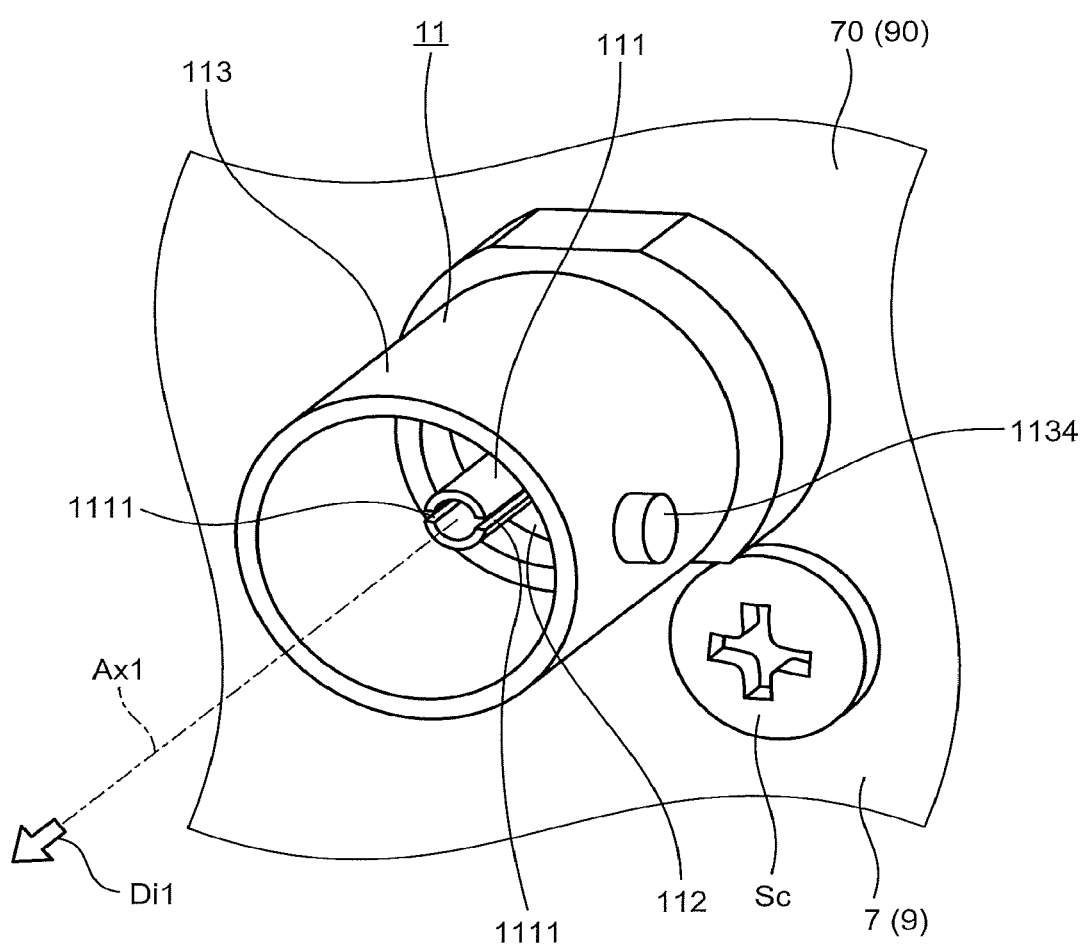
FIG. 2 is a diagram illustrating a configuration of jack connectors illustrated in FIG. 1.

In the display device 7, a jack connector 11 (FIG. 1) is installed in an exposed manner from the outside face of an outer housing 70 (see FIG. 2). The jack connector 11 is a BNC-type coaxial connector and functions as an other-side medical coaxial connector.

Regarding a detailed configuration of the jack connector 11, the explanation is given later.

The second transmission cable 8 is a BNC-type coaxial cable and functions as a medical coaxial cable. As illustrated in FIG. 1, the second transmission cable includes a coaxial cable main body 12 and plug connectors 13 that are installed at both ends of the coaxial cable main body 12.

The plug connectors 13 are BNC-type coaxial connectors and function as medical coaxial connectors.

Regarding a detailed configuration of the plug connectors 13, the explanation is given later.

The control device 9 functions as a medical signal processing device.

In an identical manner to the display device 7, in the control device 9 too, the jack connector 11 (FIG. 1) is installed in an exposed manner from the outside face of an outer housing 90 (see FIG. 2). When each plug connector 13 is connected to one of the jack connectors 11, the second transmission cable 8 connects the display device 7 and the control device 9 to each other, and transmits the video signals from the control device 9 to the display device 7.

The control device 9 is configured using a central processing unit (CPU) and comprehensively controls the operations of the light source device 3, the camera head 5, and the display device 7.

More particularly, the control device 9 generates video signals by performing predetermined processing with respect to the image signals obtained from the camera head 5 via the first transmission cable 6, and outputs the video signals to the display device 7 via the second transmission cable 8. Then, the display device 7 displays images based on the video signals. Moreover, the control device 9 outputs control signals to the camera head 5 and the light source device 3 via the first transmission cable 6 and the third transmission cable 10, respectively.

The third transmission cable 10 has one end thereof connected to the light source device 3 in a detachably attachable manner, and has the other end thereof connected to the control device 9 in a detachably attachable manner. The third transmission cable 10 transmits the control signals from the control device 9 to the light source device 3.

Configuration of jack connector Given below is the explanation of the jack connectors 11.

Figure 3:
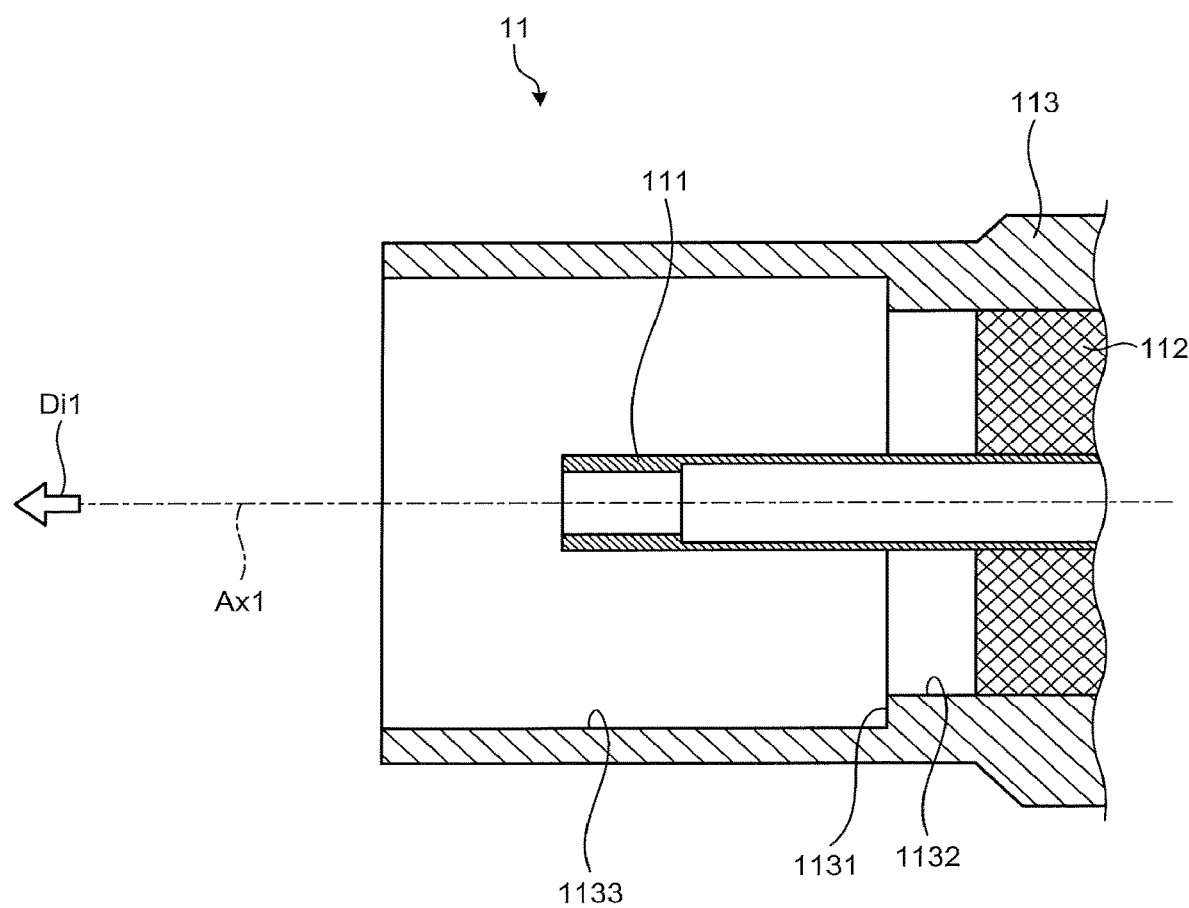
FIG. 3 is a diagram of a cross-section of the configuration of the jack connectors illustrated in FIG. 1.

FIGS. 2 and 3 are diagrams illustrating a configuration of the jack connector 11. More particularly, FIG. 2 is a perspective view of the jack connector 11, when viewed from the leading end thereof, in the state of being attached either to the outer housing 70 of the display device 7 or to the outer housing 90 of the control device 9. FIG. 3 is a cross-sectional view obtained when the jack connector 11 is cut along a cutting plane including a central axis Ax1 of a jack-side outer contact 113.

As illustrated in FIGS. 2 and 3, the jack connector 11 includes a jack-side central contact 111, a jack-side insulating base 112, and the jack-side outer contact 113.

The jack-side central contact 111 is made of an electrically conductive material and functions as an other-side inner conductor. As illustrated in FIGS. 2 and 3, the jack-side central contact 111 has a cylindrical shape and is placed to be coaxial with the central axis Ax1. Moreover, the jack-side central contact 111 is electrically connected to the circuit inside either the display device 7 or the control device 9.

As illustrated in FIG. 2, in the jack-side central contact 111, a plurality of slits 1111, which extends from the leading end toward the base end in a connection direction Di1 leading to the plug connector 13, is provided in the circumferential direction. Because of the slits 1111, the leading end side of the jack-side central contact 111 becomes elastically deformable in the direction of moving close to and moving away from the central axis Ax1 with the base end side serving as the fulcrum point.

The jack-side insulating base 112 is made of an insulating material and, as illustrated in FIG. 3, is cylindrical in shape having a substantially identical inner diameter to the outer diameter of the jack-side central contact 111. The jack-side central contact 111 is fit in the jack-side insulating base 112. In that state, the leading end in the connection direction Di1 of the jack-side central contact 111 protrudes more in the connection direction Di1 as compared to the jack-side insulating base 112.

The jack-side outer contact 113 is made of an electrically conductive material and functions as an other-side outer conductor. As illustrated in FIGS. 2 and 3, the jack-side outer contact 113 has a cylindrical shape and supports the jack-side central contact 111 at the inner periphery of the base end side via the jack-side insulating base 112 in such a way that the jack-side central contact 111 becomes coaxial with the central Ax1. That is, the jack-side outer contact 113 is electrically insulated from the jack-side central contact 111 because of the jack-side insulating base 112. In that state, the leading end in the connection direction Di1 of the jack-side outer contact 113 protrudes more in the connection direction Di1 as compared to the jack-side central contact 111.

The inner periphery of the jack-side outer contact 113 has a greater diameter at the leading end side than the diameter at the base end side. That is, as illustrated in FIG. 3, on the inner periphery of the jack-side outer contact 113, a step portion 1131 that is flat in nature is formed in an orthogonal manner to the central axis Ax1. In the following explanation, the inner periphery on the base end side with respect to the step portion 1131 is referred to as an inner periphery 1132 (FIG. 3), and the inner periphery on the leading end side with respect to the step portion 1131 is referred to as an inner periphery 1133 (FIG. 3).

On the outer periphery of the jack-side outer contact 113, two protrusions 1134 that protrude outward are formed at mutually opposite positions as illustrated in FIG. 2. In FIG. 2, only one of the two protrusions 1134 is visible.

Moreover, on the outer periphery of the jack-side outer contact 113, a flange (not illustrated) that is flared outward and that is used for fixing the jack connector 11 to either the outer housing 70 or the outer housing 90 using a screw Sc (FIG. 2).

Configuration of plug connector Given below is the explanation of the plug connector 13.

Figure 4:
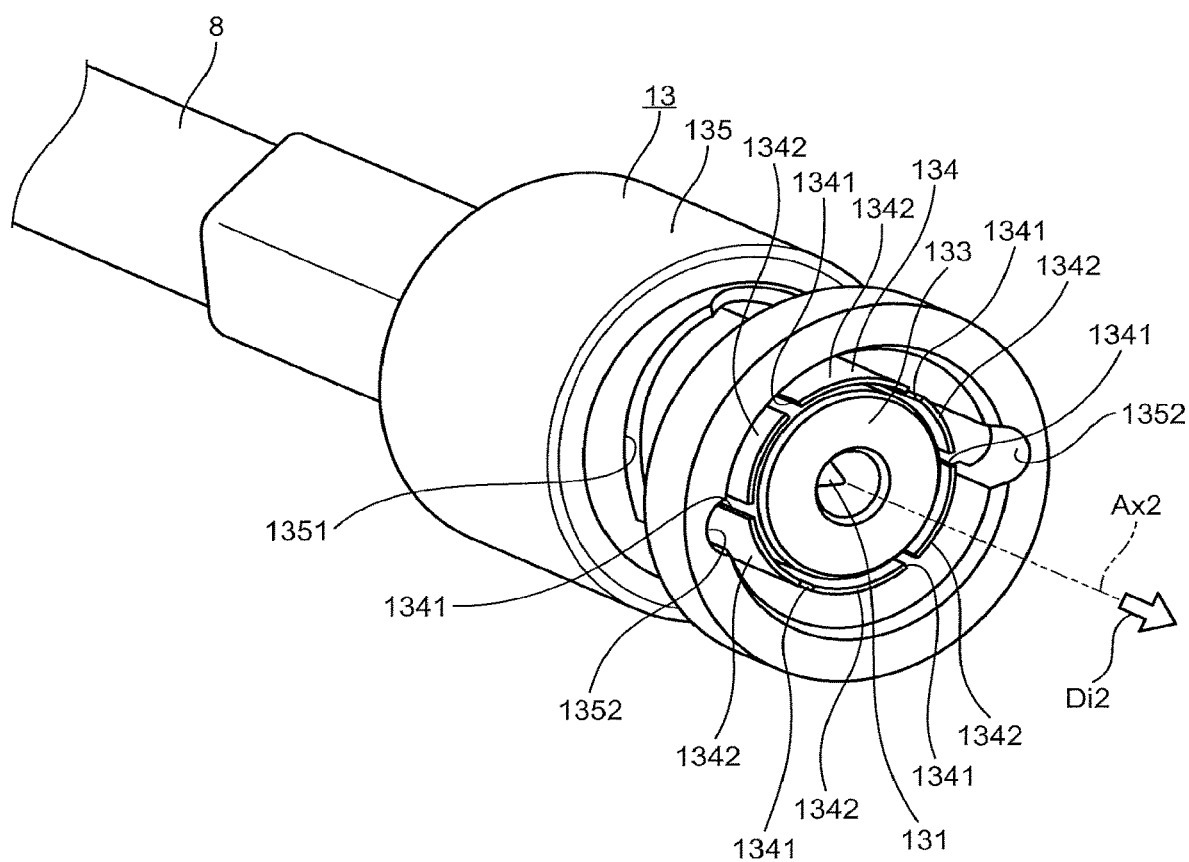
FIG. 4 is a diagram illustrating a configuration of plug connectors illustrated in FIG. 1.
Figure 5:
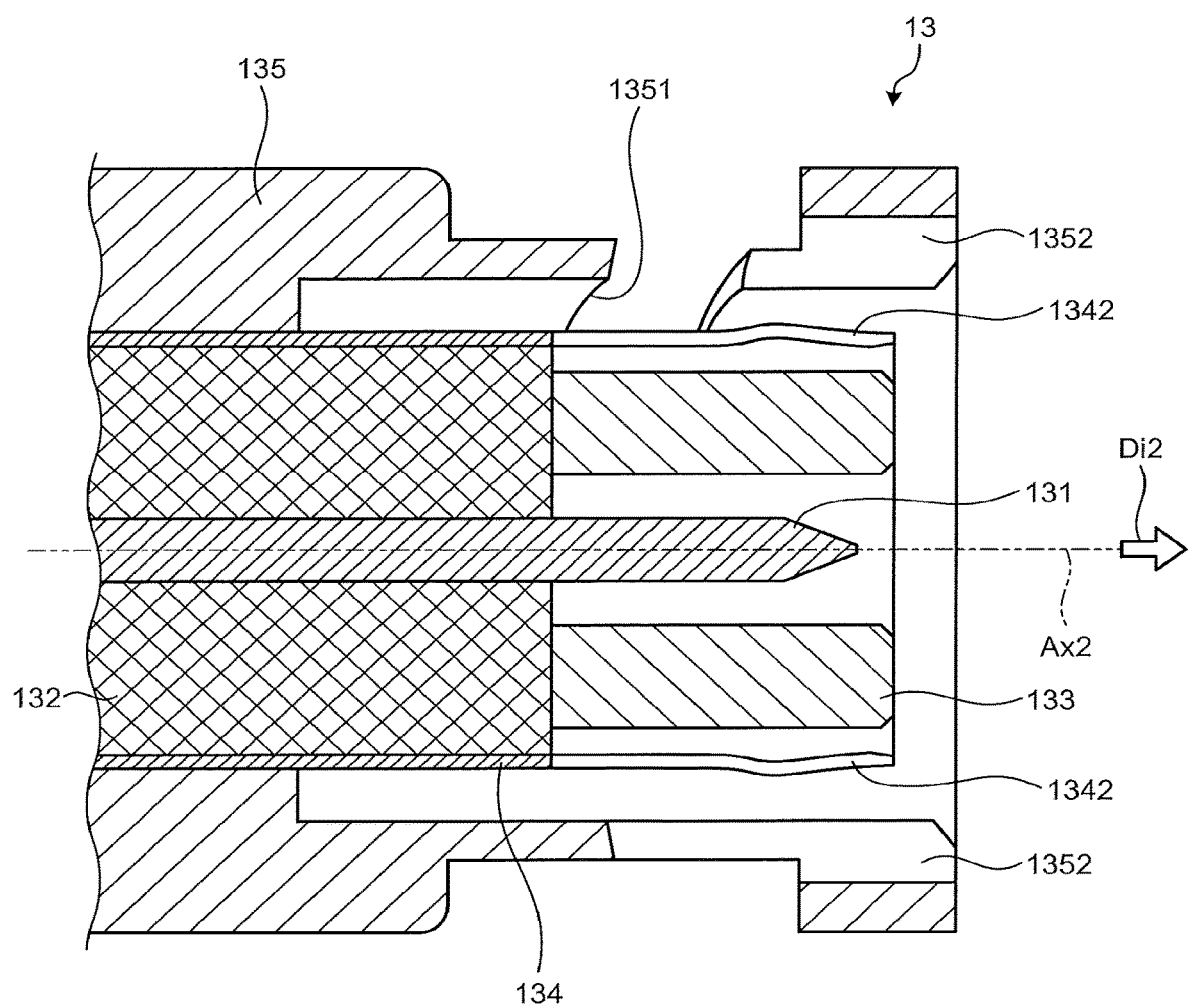
FIG. 5 is a diagram of a cross-section of the configuration of the plug connectors illustrated in FIG. 1.

FIGS. 4 and 5 are diagrams illustrating a configuration of the plug connector 13. More particularly, FIG. 4 is a perspective view of the plug connector 13 that is attached to one end of the second transmission cable 8. FIG. 5 is a cross-sectional view obtained when the plug connector 13 is cut along a cutting plane including a central axis Ax1 of the second transmission cable 8.

As illustrated in FIGS. 4 and 5, the plug connector 13 includes a plug-side central contact 131, a plug-side insulating base 132 (FIG. 5), an insulating wall 133, a cylindrical portion 134, and a plug-side outer contact 135.

The plug-side central contact 131 is made of an electrically conductive material and functions as an inner conductor. The plug-side central contact 131 has the leading end tapering in a connection direction Di2 toward the jack connector 11, and is configured using a substantially columnar pin having a slightly greater outer diameter than the inner diameter of the jack-side central contact 111. Moreover, the plug-side central contact 131 is fixed to the second transmission cable 8 in a coaxial manner to the central axis Ax2 and is electrically connected to the signal line in the second transmission cable 8.

The plug-side insulating base 132 is made of an insulating material and is cylindrical in shape having a substantially identical inner diameter to the outer diameter of the plug-side central contact 131 and having a smaller outer diameter than the inner diameter of the inner periphery 1133 of the jack-side outer contact 113. The plug-side insulating base 132 is fixed to the second transmission cable 8 with the plug-side central contact 131 being inserted (fit) therein. In that state, the leading end in the connection direction Di2 of the plug-side central contact 131 protrudes more in the connection direction Di2 as compared to the plug-side insulating base 132.

The insulating wall 133 is made of an insulating material and functions as an insulating body. The insulating wall 133 is cylindrical in shape having a greater inner diameter than the outer diameter of the jack-side central contact 111 and having a smaller outer diameter than the outer diameter of the plug-side insulating base 132. The insulating wall 133 is fixed to the leading end in the connection direction Di2 of the plug-side insulating base 132 with the plug-side central contact 131 being inserted therein (while surrounding the plug-side central contact 131) and in a coaxial manner with the plug-side central contact 131. In that state, the leading end in the connection direction Di2 of the insulating wall 133 protrudes more in the connection direction Di2 as compared to the plug-side central contact 131.

The cylindrical portion 134 is made of an electrically conductive material and is cylindrical in shape having a substantially identical inner diameter to the outer diameter of the plug-side insulating base 132 and having a substantially identical outer diameter to the inner diameter of the inner periphery of the jack-side outer contact 113. The cylindrical portion 134 is fixed to the second transmission cable 8 with the plug-side insulating base 132 being inserted (fit) therein and having the plug-side central contact 131, the plug-side insulating base 132, and the insulating wall 133 arranged on the inner periphery side thereof. In that state, the leading end in the connection direction Di2 of the cylindrical portion 134 has a substantially identical protruding position to that of the leading end in the connection direction Di2 of the insulating wall 133. Moreover, in the state of being electrically insulated from the plug-side insulating base 132 and the insulating wall 133, the cylindrical portion 134 gets electrically connected to a shield casing (ground line) of the second transmission cable 8.

As illustrated in FIG. 4, in the cylindrical portion 134, a plurality of (in the first embodiment, six) slits 1341, which extends from the leading end toward the base end in the connection direction Di2 up to the substantially same position as the position of the leading end of the plug-side insulating base 132, is provided in the circumferential direction. Because of the slits 1341, the leading end side in the connection direction Di2 of the cylindrical portion 134 functions as six leaf springs 1342 that are elastically deformable in the direction of moving close to and moving away from the central axis Ax2 with the base end side serving as the fulcrum point.

Regarding the cylindrical shape formed by the six leaf springs 1342, more toward the leading end side of the connection direction Di2, the inner diameter becomes slightly greater than the inner diameter of the inner periphery 1133 of the jack-side outer contact 113 and then becomes curved and slightly smaller than the inner diameter of the inner periphery 1133.

The plug-side outer contact 135 is made of an electrically conductive material and functions as an outer conductor. The plug-side outer contact 135 is cylindrical in shape having a greater inner diameter than the outer diameter of the jack-side outer contact 113. Moreover, the plug-side outer contact 135 is attached to the second transmission cable 8 in a rotatable manner around the central axis Ax2 and in a coaxial manner with the central axis Ax2 with the plug-side central contact 131, the plug-side insulating base 132, the insulating wall 133, and the cylindrical portion 134 arranged on the inner periphery side thereof. In that state, the leading end in the connection direction Di2 of the plug-side outer contact 135 protrudes more in the connection direction Di2 as compared to the cylindrical portion 134. In an identical manner to the cylindrical portion 134, the plug-side outer contact 135 is electrically connected to the shield casing (ground line) of the second transmission cable 8 while being electrically isolated from the plug-side central contact 131 because of the plug-side insulating base 132 and the insulating wall 133.

As illustrated in FIGS. 4 and 5, on the lateral face of the plug-side outer contact 135, two grooves 1351 that extend in a helical manner around the central axis Ax2 are formed at mutually opposite positions. In FIG. 2, only one of the two grooves 1351 is visible.

Moreover, as illustrated in FIGS. 4 and 5, on the inner periphery of the plug-side outer contact 135, two recessed grooves 1352 that extend from the leading end toward the base end in the connection direction Di2 and that are communicated with the two grooves 1351 are formed at mutually opposite positions.

Operation of Connecting Plug Connector to Jack Connector

Figure 6:
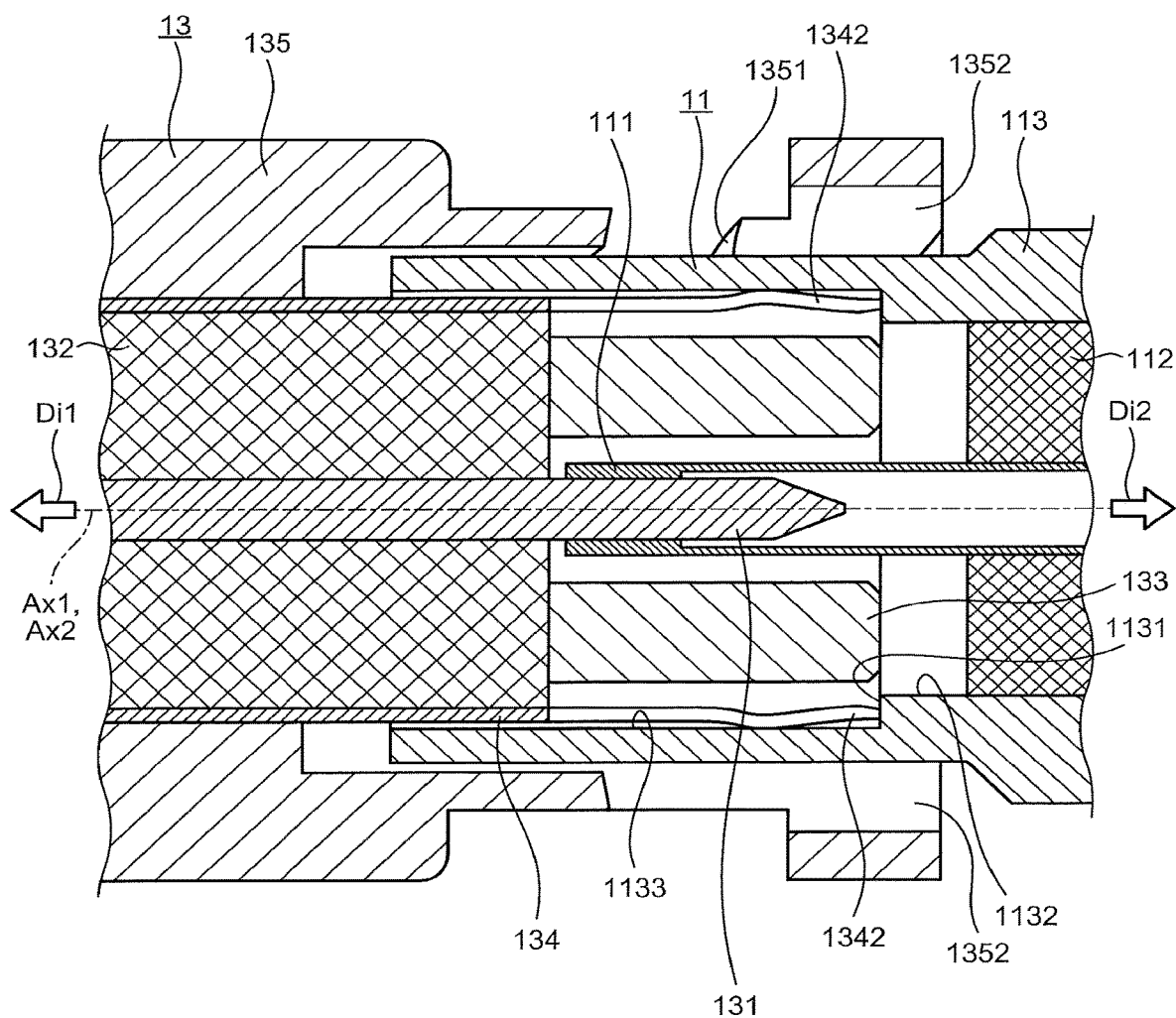
FIG. 6 is a diagram illustrating a cross-section of the state in which the jack connector illustrated in FIG. 2 is connected to the plug connector illustrated in FIG. 5.

FIG. 6 is a diagram illustrating a cross-section of the state in which the jack connector 11 and the plug connector 13 are connected to each other. More particularly, FIG. 6 is a cross-sectional view corresponding to FIGS. 3 and 5.

The operation of connecting the plug connector 13 to the jack connector 11 is performed as explained below.

Firstly, the operator matches the two recessed grooves 1352 with the two protrusions 1134, and inserts the plug connector 13 in the connection direction Di2.

As a result, the plug-side central contact 131 gets inserted inside the jack-side central contact 111 while elastically deforming the jack-side central contact 111 to the outer periphery side. Moreover, the six leaf springs 1342 get inserted inside the jack-side outer contact 113 until their leading ends abut against the step portion 1131 in the connection direction Di2 while getting elastically deformed to the inner periphery side due to the jack-side outer contact 113.

The two protrusions 1134 get inserted along the two recessed grooves 1352 and enter the two grooves 1351. The jack-side outer contact 113 gets inserted in the gap between the plug-side outer contact 135 and the cylindrical portion 134.

When the two protrusions 1134 abut against the side wall of the two grooves 1351 thereby resulting in the locking of the insertion of the plug connector 13 in the connection direction Di2, the operator rotates the plug-side outer contact 135.

As a result, the two protrusions 1134 move along the two grooves 1351, and the plug connector 13 gets connected to the jack connector 11.

Once the plug connector 13 and the jack connector 11 get connected to each other as described above, the plug-side central contact 131 gets electrically connected to the jack-side central contact 111 as illustrated in FIG. 6.

Moreover, the plug-side outer contact 135 and the cylindrical portion 134 get electrically connected with the jack-side outer contact 113.

The first embodiment described above enables achieving the following effects.

Figure 7:
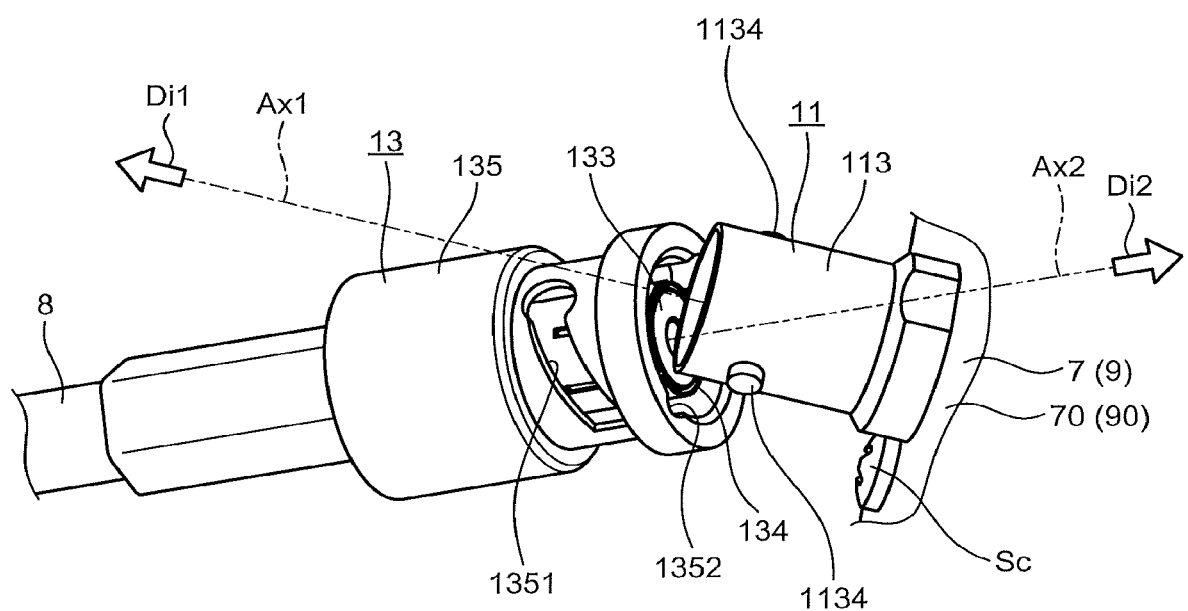
FIG. 7 is a diagram for explaining the effects of the first embodiment.
Figure 8:
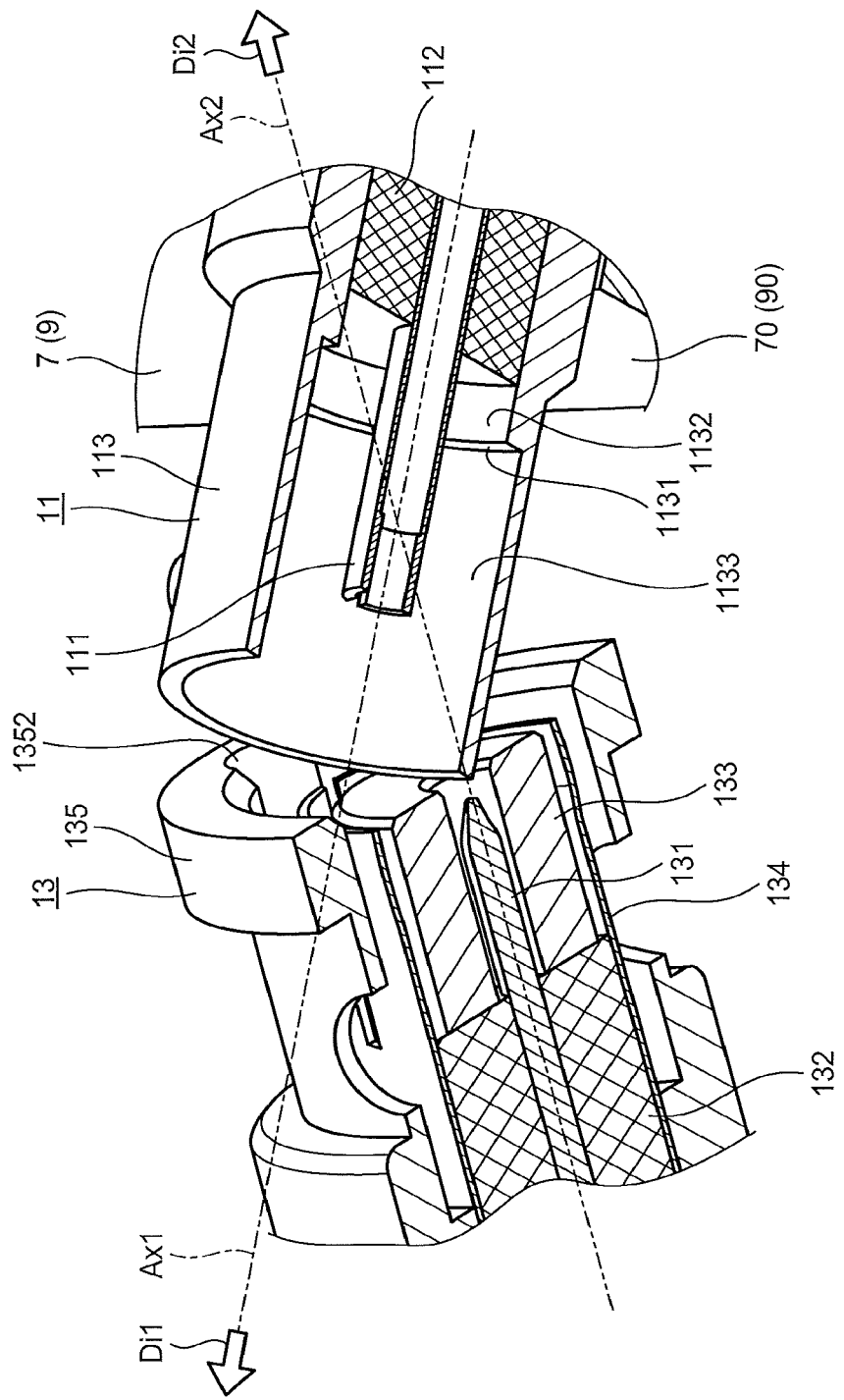
FIG. 8 is a diagram of a cross-section for explaining the effects of the first embodiment.
Figure 14:
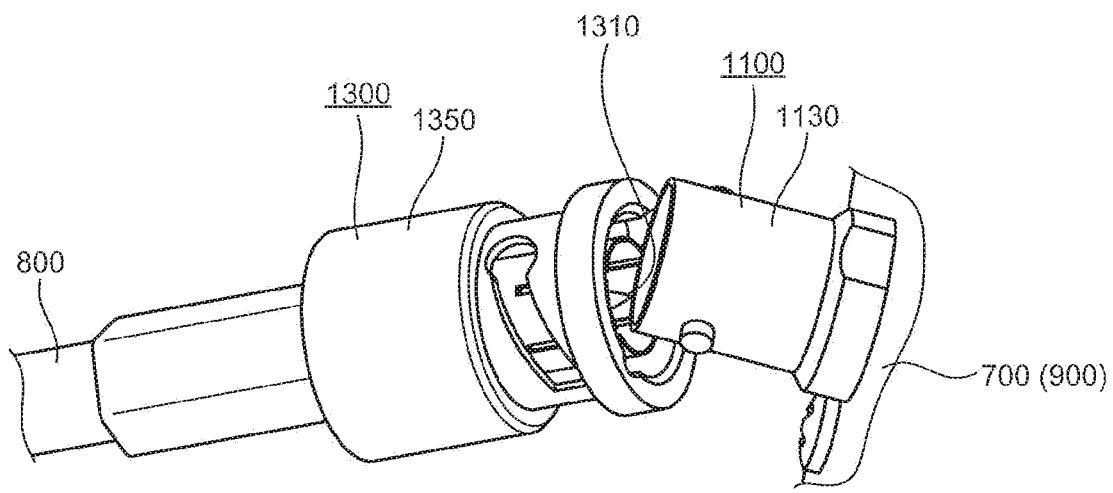
FIG. 14 is a diagram for explaining the issues faced in the medical observation system.
Figure 15:
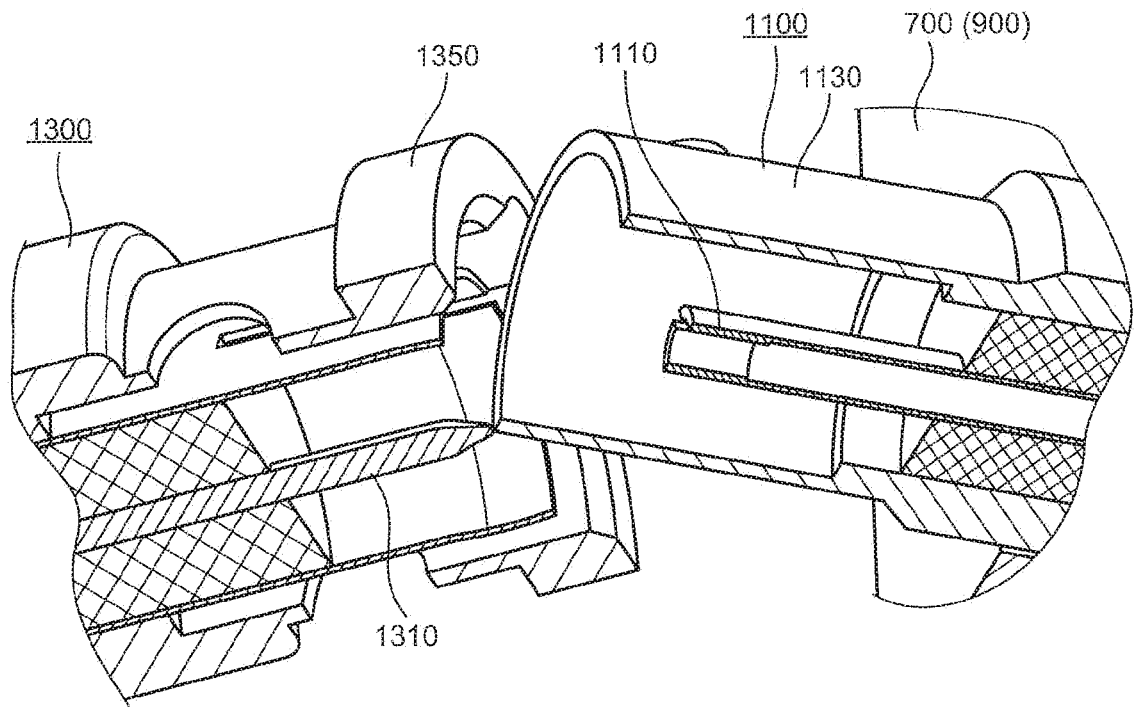
FIG. 15 is diagram of a cross-section for explaining the issues faced in the medical observation system.

FIGS. 7 and 8 are diagrams for explaining the effects of the first embodiment. FIG. 7 is a diagram corresponding to FIG. 14, and illustrates the state in which the plug connector 13 is connected to the jack connector 11. FIG. 8 is a diagram corresponding to FIG. 15, and represents an enlarged cross-sectional view of FIG. 7.

In the plug connector 13 according to the first embodiment, in between the plug-side central contact 131 and the plug-side outer contact 135, the cylindrical insulating wall 133 that surrounds the plug-side central contact 131 is provided. When the plug connector 13 is connected to the jack connector 11, the insulating wall 133 is positioned on the inner periphery side of the jack-side outer contact 113; and the leading end in the connection direction Di2 of the insulating wall 133 protrudes more in the connection direction Di2 as compared to the plug-side central contact 131.

Hence, as illustrated in FIGS. 7 and 8, when the plug connector 13 is inserted in (pressed at a slant against) the jack connector 11 in the state in which the connection directions Di1 and Dig intersect with each other, the jack-side outer contact 113 makes contact not with the plug-side central contact 131 but with the insulating wall 133. That is, the insulating wall 133 serves as an obstacle that prevents the jack-side outer contact 113 from making contact with the plug-side central contact 131. Thus, according to the first embodiment, when the plug connector 13 gets connected to the jack connector 11, it becomes possible to avoid contact between the jack-side outer contact 113 and the plug-side central contact 131. That is, in the state in which the second transmission cable 8 (one of the plug connectors 13) is connected to the control device 9 (the jack connector 11), even if the remaining plug connector 13 is pressed at a slant against the display device 7 (the jack connector 11), it becomes possible to avoid contact between the jack-side outer contact 113 and the plug-side central contact 131. Hence, there is no risk of damaging the circuit in the control device 9 due to electrostatic discharge.

Meanwhile, the plug-side outer contact 135 has a greater diameter than the jack-side outer contact 113. Hence, at the time of connecting the plug connector 13 to the jack connector 11, the plug-side outer contact 135 does not easily come in contact with the jack-side central contact 111. On the other hand, the jack-side outer contact 113 may easily make contact with the plug-side central contact 131.

In the first embodiment, the insulating wall 133 is provided in the plug connector 13. Hence, from among the pair of the plug-side outer contact 135 and the jack-side central contact 111 and the pair of the jack-side outer contact 113 and the plug-side central contact 131, the insulating wall 133 effectively enables avoiding contact between the jack-side outer contact 113 and the plug-side central contact 131 that may easily come in contact with each other.

Meanwhile, in the second transmission cable 8, assume that the insulating wall 133 is provided in only one of the two plug connectors 13 installed at both ends of the coaxial cable main body 12. In that case, for example, in case the operator mistakenly connects the plug connector 13 having the insulating wall 133 to the control device 9 (the jack connector 11) and then connects the plug connector 13 not having the insulating wall 133 to the display device 7 (the jack connector 11), then there is a risk that the jack-side outer contact 113 comes in contact with the plug-side central contact 131.

In contrast, in the second transmission cable 8 according to the first embodiment, since the insulating wall 133 is provided in each of the two plug connectors 13 installed at both ends of the coaxial cable main body 12, the above-mentioned issue does not arise.

Second Embodiment

Given below is the explanation of a second embodiment. In the following explanation, the constituent elements identical to the first embodiment are referred to by the same reference numerals, and their explanation is either not repeated or given only in brief.

In the first embodiment, the present disclosure is implemented in the medical observation system 1 in which a rigid endoscope (the inserting unit 2) is used.

In the second embodiment, the present disclosure is implemented in a medical observation system in which, what is called, a videoscope is used that has an imaging unit at the leading end side of the inserting unit.

Figure 9:
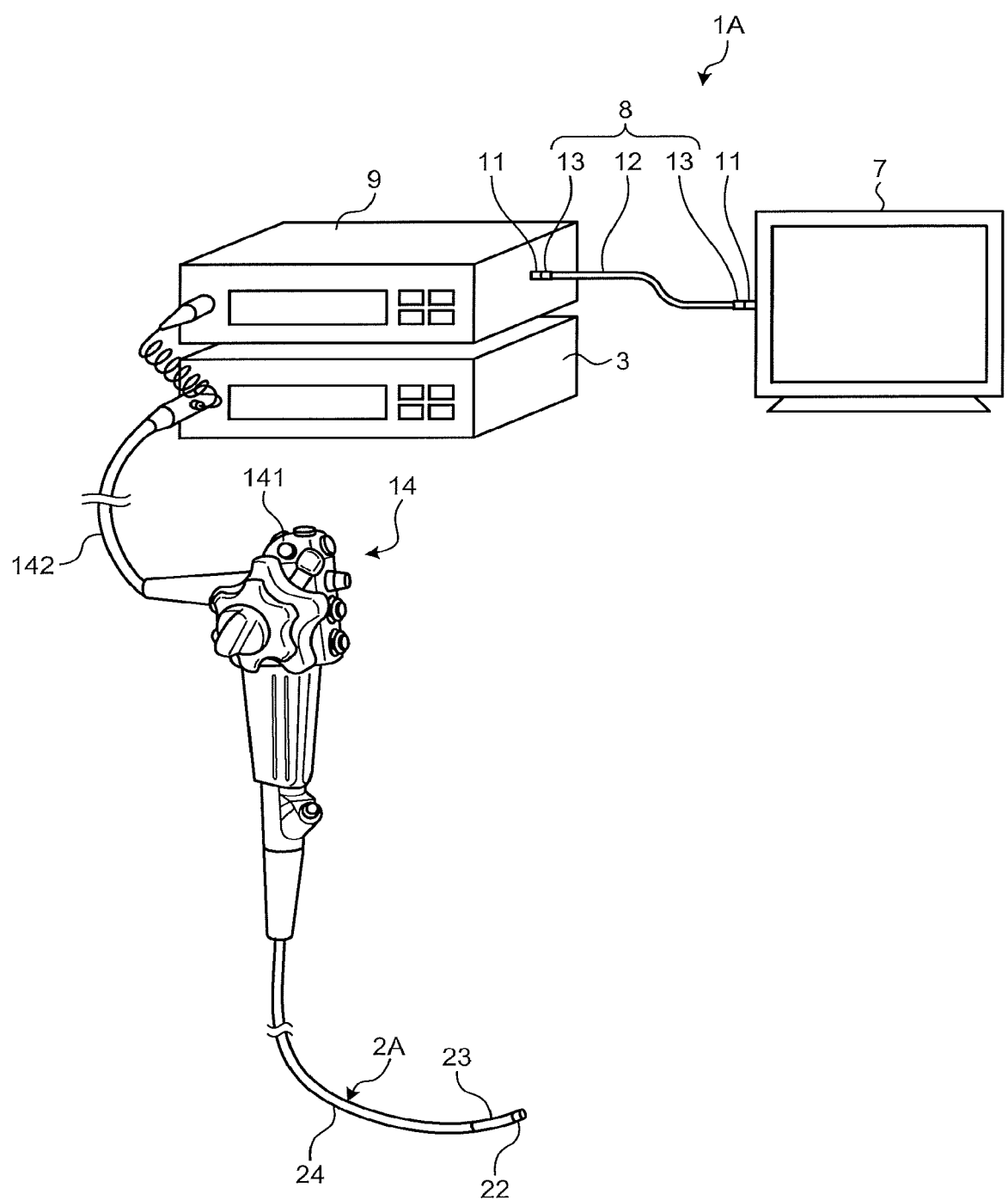
FIG. 9 is a diagram illustrating an overall configuration of a medical observation system according to a second embodiment.

FIG. 9 is a diagram illustrating an overall configuration of a medical observation system 1A according to the second embodiment.

As illustrated in FIG. 9, the medical observation system 1A according to the second embodiment includes: an endoscope 14 that, when an inserting unit 2A thereof is inserted inside a body, takes in-body images of the body parts being observed and outputs image signals; the light source device 3 that generates illuminating light which is emitted from the leading end of the endoscope 14; the control device 9 that processes the image signals output from the endoscope 14, and generates and outputs video signals; the display device 7 that displays images based on the video signals; and the second transmission cable 8 that connects the control device 9 and the display device 7 using the jack connectors 11 and the plug connectors 13, and transmits the video signals from the control device 9 to the display device 7.

As illustrated in FIG. 9, the endoscope 14 includes the inserting unit 2A that is elongated in shape and flexible in nature; an operating unit 141 that is connected to the base end side of the inserting unit 2A and that receives input of various operation signals; and a universal cord 142 that extends in a different direction than the direction of extension of the inserting unit 2A from the operating unit 141 and has various built-in cables for connecting with the light source device 3 and the control device 9.

As illustrated in FIG. 9, the inserting unit 2A includes a leading end portion 22 in which an imaging unit (not illustrated) is built-in for taking images of the inside of the body and generating image signals; a freely-bendable bending portion 23 that is connected to the base end side of the leading end portion 22 and that is made of a plurality of bending pieces; and a flexible tube portion 24 that is long and flexible. The image signals obtained by imaging by the leading end portion 22 (the imaging unit) are output to the control device 9 via the operating unit 141 and the universal cord 142.

Even in the case of using a flexible endoscope (the endoscope 14) as explained in the second embodiment, it is possible to achieve the same effects as those achieved in the first embodiment.

Third Embodiment

Given below is the explanation of a third embodiment. In the following explanation, the constituent elements identical to the first embodiment are referred to by the same reference numerals, and their explanation is either not repeated or given only in brief.

In the first embodiment, the present disclosure is implemented in the medical observation system 1 in which a rigid endoscope (the inserting unit 2) is used.

In the third embodiment, the present disclosure is implemented in a medical observation system in which an operation microscope is used for enlarging a predetermined field of view inside the subject being examined (inside the body) or on the surface of the subject being examined (on the surface of the body).

Figure 10:
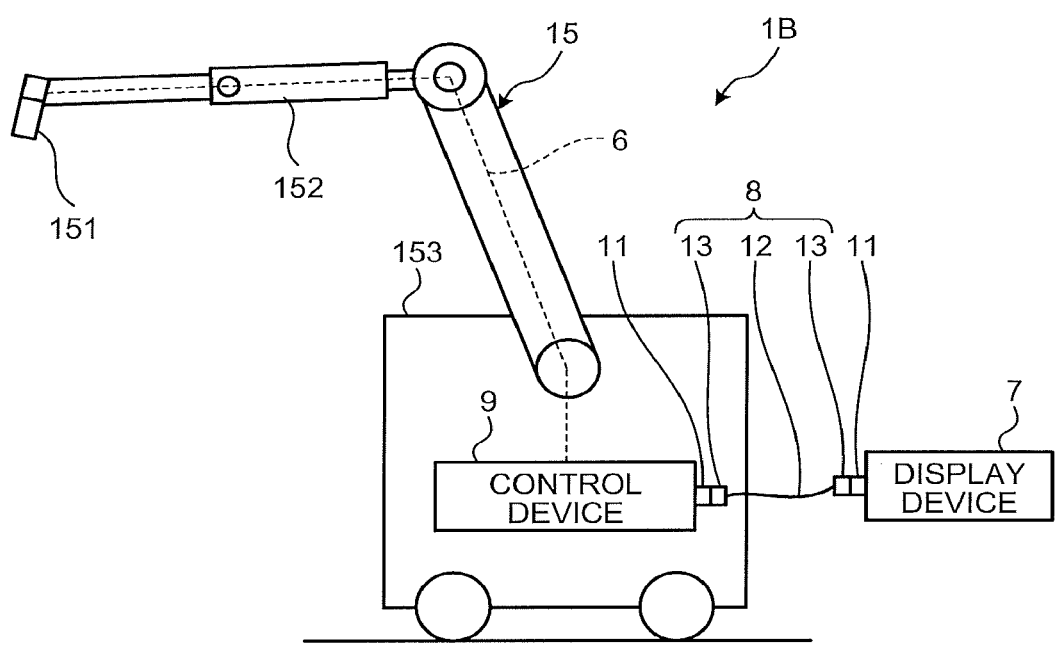
FIG. 10 is a diagram illustrating an overall configuration of a medical observation system according to a third embodiment.

FIG. 10 is a diagram illustrating an overall configuration of a medical observation system 1B according to the third embodiment.

As illustrated in FIG. 10, the medical observation system 1B according to third embodiment includes an operation microscope 15 that takes images to be used in observing the photographic subject and outputs image signals; the control device 9 that processes the image signals output from the operation microscope 15, and that generates and outputs video signals; the display device 7 that displays images based on the video signals; and the second transmission cable 8 that connects the control device 9 and the display device 7 using the jack connectors 11 and the plug connectors 13, and transmits the video signals from the control device 9 to the display device 7.

As illustrated in FIG. 10, the operation microscope 15 includes a microscope 151 that enlarges the minute body parts of the photographic subject and takes images of the enlarged portion, and outputs image signals; a supporting unit 152 that is connected to the base end portion of the microscope 151 and that includes an arm for supporting the microscope 151 in a rotatable manner; and a base portion 153 that holds the base end portion of the supporting unit 152 in a rotatable manner and that is movable on the floor.

As illustrated in FIG. 10, the control device 9 is installed in the base portion 153. Moreover, in the supporting unit 152, the first transmission cable 6 is laid along the supporting unit 152. Thus, the image signals taken by the microscope 151 are output to the control device 9 via the first transmission cable 6.

Meanwhile, instead of configuring the base portion 153 to be movable on the floor, the base portion 153 may be fixed to the ceiling or a wall surface for supporting the supporting unit 152. Moreover, the base portion 153 may also include a light source that generates illuminating light which is used to illuminate the photographic subject from the operation microscope 15.

Even in the case of using the operation microscope 15 as explained in the third embodiment, it is possible to achieve the same effects as those achieved in the first embodiment.

Other Embodiments

Although the embodiments are described above, the present disclosure is not limited by the first to third embodiments described above.

Figure 11:
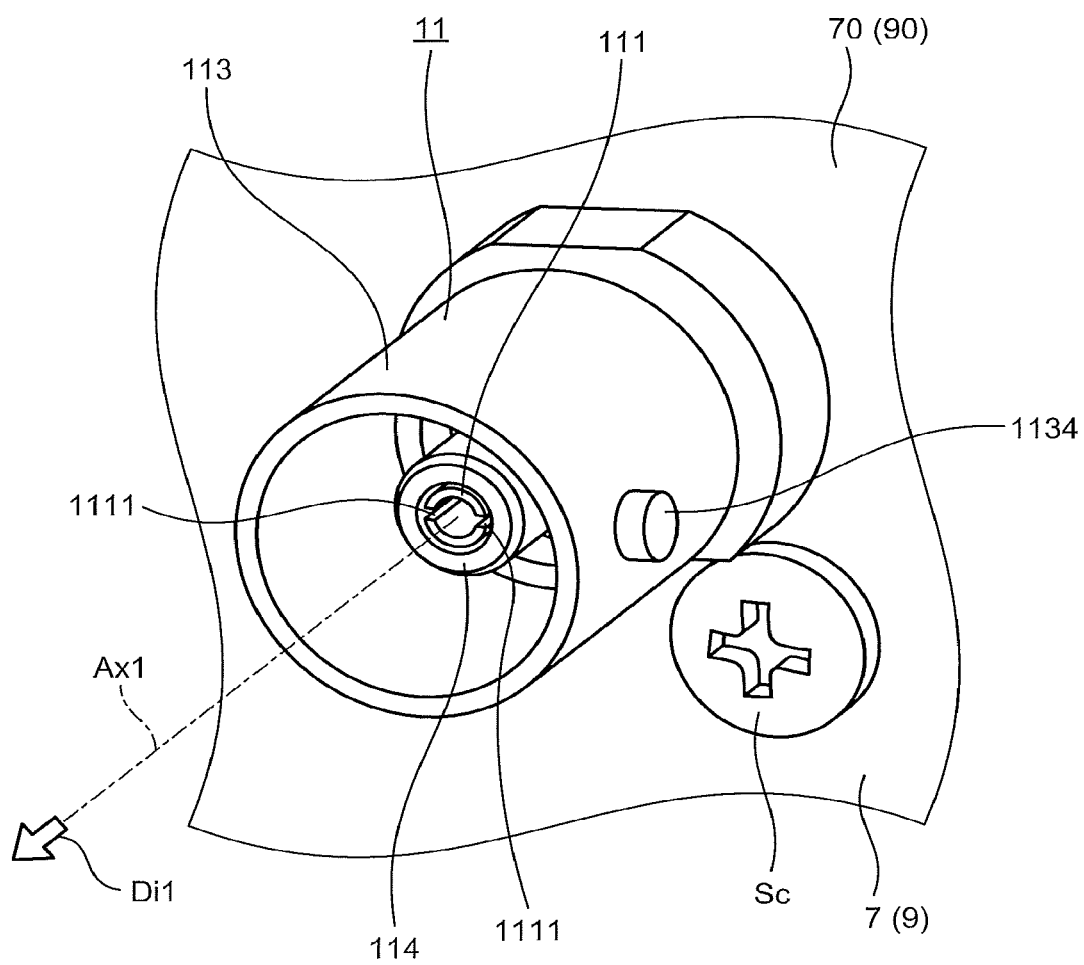
FIG. 11 is a diagram illustrating a modification example of the first to third embodiments.
Figure 12:
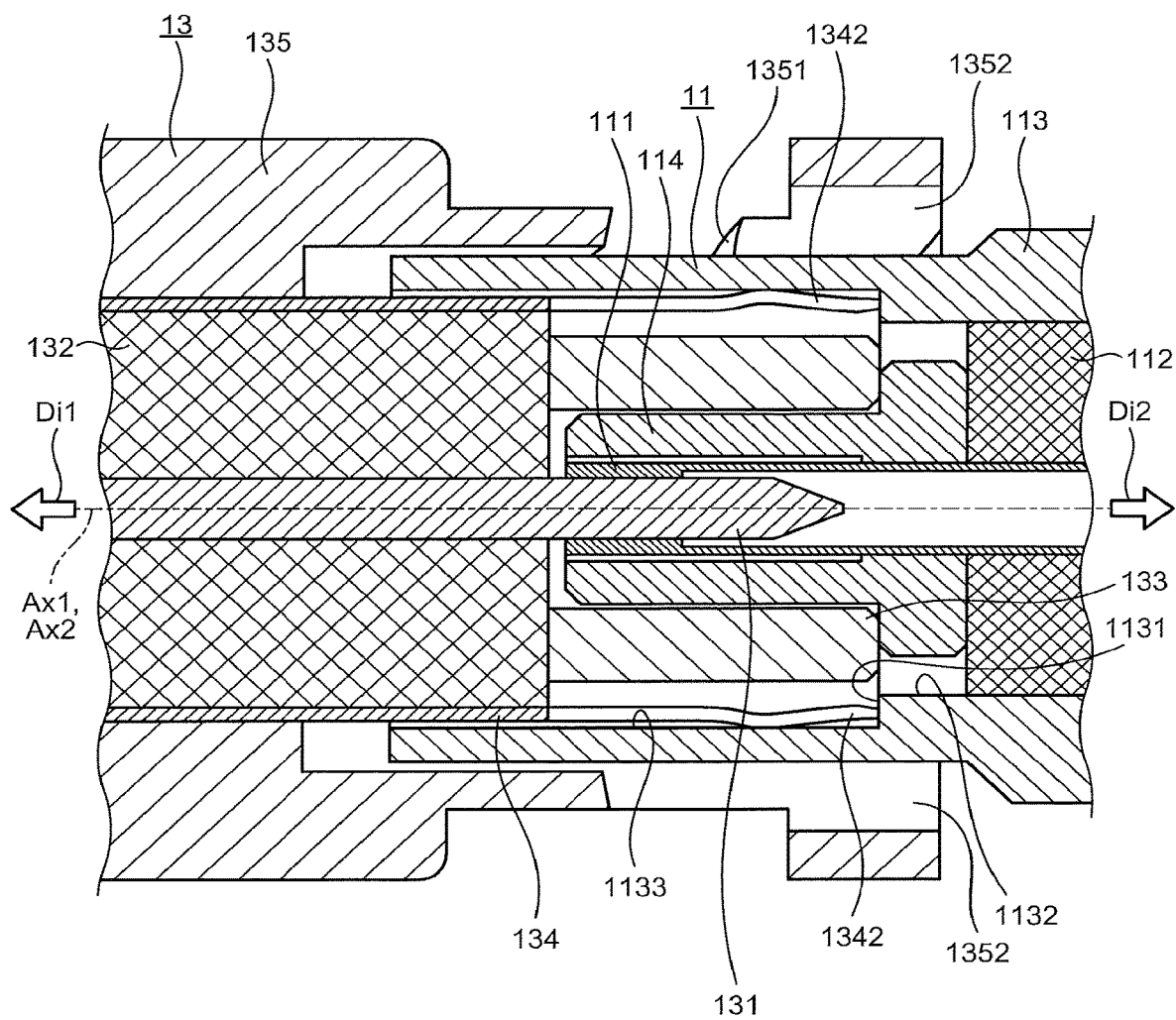
FIG. 12 is a diagram of a cross-sectional view of the modification example of the first to third embodiments.
Figure 13:
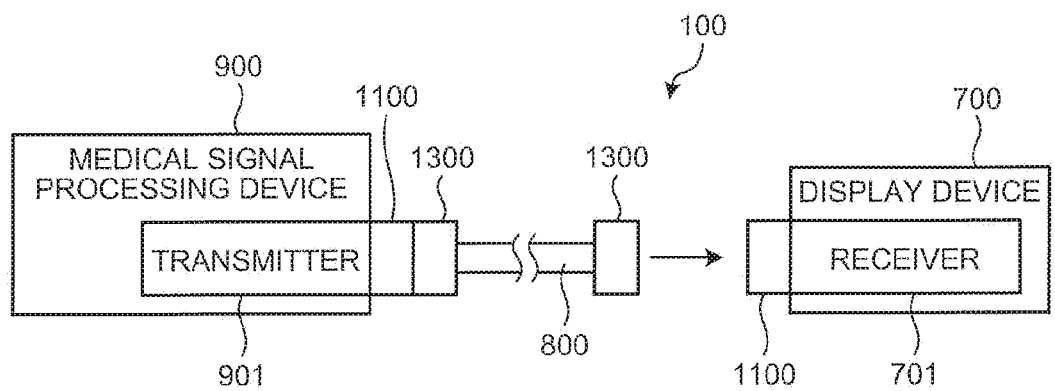
FIG. 13 is a diagram for explaining the issues faced in a medical observation system.

FIGS. 11 and 12 are diagrams illustrating a modification example of the first to third embodiments. More particularly, FIG. 11 is a diagram corresponding to FIG. 2. FIG. 12 is a cross-sectional view corresponding to FIG. 6.

In the first to third embodiments, as illustrated in FIGS. 11 and 12, it is possible to include an insulating sleeve 114 in the jack connector 11.

The insulating sleeve 114 is made of an insulating material and, as illustrated in FIGS. 11 and 12, is cylindrical in shape having a slightly greater inner diameter than the outer diameter of the jack-side central contact 111 and having a smaller outer diameter than the inner diameter of the insulating wall 133. The insulating sleeve 114 is fixed to the leading end in the connection direction Di1 of the jack-side insulating base 112 with the jack-side central contact 111 being inserted (fit) therein. In that state, the leading end in the connection direction Di1 of the insulating sleeve 114 has a substantially identical protruding position to that of the leading end in the connection direction Di1 of the jack-side central contact 111. When the plug connector 13 is inserted in the jack connector 11, the insulating sleeve 114 gets inserted inside the insulating wall 133.

According to the modification example, in addition to achieving the same effects as the effects achieved in the first to third embodiment, the insulating sleeve 114 may prevent the jack-side central contact 111 from breaking and bending.

In the first to third embodiments, the plug-side central contact 131 in the plug connector 13 may be configured to have an identical shape to the shape of the jack-side central contact 111, and the jack-side central contact 111 in the jack connector 11 may be configured to have an identical shape to the shape of the plug-side central contact 131.

In the first to third embodiments, the insulating wall 133 may be provided alternatively in each jack connector 11. In that case too, it is desirable that the leading end in the connection direction Di1 of the insulating wall 133 protrudes more in the connection direction Di1 as compared to the jack-side central contact 111.

In the first to third embodiments, as the jack connectors 11 and the plug connectors 13, it is possible to use, what are called, active BNCs that have a built-in cable driver and a built-in equalizer.

In the medical coaxial connector according to the present disclosure, in between the inner conductor and the outer conductor is provided a tubular insulating body that surrounds the inner conductor. When the medical coaxial connector is connected to the other-side medical coaxial connector, the insulating body is placed on the inner periphery side of the other-side outer conductor, and the leading end of the insulating body in the connection direction toward the other-side medical coaxial connector protrudes more in the connection direction as compared to the inner conductor.

Hence, when the medical coaxial connector is pressed at a slant against the other-side medical coaxial connector, the other-side outer conductor makes contact not with the inner conductor but with the insulating body. That is, the insulating body serves as an obstacle that prevents the other-side outer conductor from making contact with the inner conductor. Thus, in the medical coaxial connector according to the present disclosure, at the time of connecting with the other-side medical coaxial connector, it becomes possible to avoid contact between the other-side outer conductor and the inner conductor.

Moreover, since the medical coaxial cable and the medical observation system according to the present disclosure include the medical coaxial connector described above, it becomes possible to achieve the same behavior and the same effects as the medical coaxial connector.

It should be understood by those skilled in the art that various modifications, combinations, sub-combinations and alterations may occur depending on design requirements and other factors insofar as they are within the scope of the appended claims or the equivalents thereof.

What is claimed is:

1. A medical coaxial connector of a Bayonet Neill Concelman type adapted to be connected to an other-side medical coaxial connector, and transmit to the other-side medical coaxial connector a video signal according to examination results of a subject,
the other-side medical coaxial connector including
an other-side inner conductor, and
an other-side outer conductor electrically insulated from the other-side inner conductor and formed in a tubular shape surrounding the other-side inner conductor,
the medical coaxial connector comprising:
an internal conductor configured to be electrically connected to the other-side inner conductor when the medical coaxial connector is connected to the other-side medical coaxial connector;
an outer conductor electrically insulated from the internal conductor, formed in a tubular shape surrounding the internal conductor, and configured to be electrically connected to the other-side outer conductor when the medical coaxial connector is connected to the other-side medical coaxial connector;
an insulating body that is placed on inner periphery side of the outer conductor and formed in a cylindrical shape surrounding the internal conductor; and
a cylindrical portion provided between the outer conductor and the insulating body,
wherein the insulating body is configured to be placed on inner periphery side of the other-side outer conductor and a leading end of the insulating body in a connection direction toward the other-side coaxial connector is configured to protrude more in the connection direction than the internal conductor when the medical coaxial connector is connected to the other-side medical coaxial connector,
wherein the cylindrical portion is configured to be electrically connected to the outer conductor and inner periphery surface of the other-side outer conductor when the medical coaxial connector is connected to the other-side medical coaxial connector, and
wherein the cylindrical portion is configured to protrude a substantially same distance in the connection direction as the insulating body.

2. The medical coaxial connector according to claim 1, wherein the outer conductor is configured to position on outer periphery side of the other-side outer conductor when the medical coaxial connector is connected to the other-side medical coaxial connector.

3. A medical coaxial cable adapted to transmit a video signal according to examination results of a subject, the medical coaxial cable comprising:
a coaxial cable main body that transmits the video signal; and
the medical coaxial connectors according to claim 1 that are installed at both ends of the coaxial cable main body.

4. A medical observation system comprising:
a medical signal processing device configured to output a video signal according to examination results of a subject;
a display device configured to display an image based on the video signal; and
the medical coaxial cable according to claim 3 that connects the medical signal processing device and the display device, and that transmits the video signal from the medical signal processing device to the video signal, wherein
the medical signal processing device and the display device each include the other-side medical coaxial connector configured to be connected to the medical coaxial connector installed at one of both ends of the medical coaxial cable.

5. The medical coaxial connector according to claim 1, wherein the insulating body and the cylindrical portion are spaced apart from each other in a radial direction.

6. The medical coaxial connector according to claim 1, wherein the cylindrical portion has a plurality of slits extending from the leading end to a base end.

7. A medical coaxial connector of a Bayonet Neill Concelman type adapted to be connected to an other-side medical coaxial connector, and transmit to the other-side medical coaxial connector a video signal according to examination results of a subject,
the other-side medical coaxial connector including
an other-side inner conductor, and
an other-side outer conductor electrically insulated from the other-side inner conductor and formed in a tubular shape surrounding the other-side inner conductor,
the medical coaxial connector comprising:
an internal conductor configured to be electrically connected to the other-side inner conductor when the medical coaxial connector is connected to the other-side medical coaxial connector;
an outer conductor electrically insulated from the internal conductor, formed in a tubular shape surrounding the internal conductor, and configured to be electrically connected to the other-side outer conductor when the medical coaxial connector is connected to the other-side medical coaxial connector;
an insulating body that is placed on inner periphery side of the outer conductor and formed in a cylindrical shape surrounding the internal conductor; and
a cylindrical portion provided between the outer conductor and the insulating body,
wherein the insulating body is configured to be placed on inner periphery side of the other-side outer conductor and a leading end of the insulating body in a connection direction toward the other-side coaxial connector is configured to protrude more in the connection direction than the internal conductor when the medical coaxial connector is connected to the other-side medical coaxial connector,
wherein the cylindrical portion is configured to be electrically connected to the outer conductor and inner periphery surface of the other-side outer conductor when the medical coaxial connector is connected to the other-side medical coaxial connector, and
wherein a leading end of the other-side outer conductor in a connection direction toward the medical coaxial connector is configured to protrude more in the connection direction toward the medical coaxial connector than the other-side inner conductor when the medical coaxial connector is connected to the other-side medical coaxial connector.

8. The medical coaxial connector according to claim 7, wherein the outer conductor is configured to position on outer periphery side of the other-side outer conductor when the medical coaxial connector is connected to the other-side medical coaxial connector.

9. A medical coaxial cable adapted to transmit a video signal according to examination results of a subject, the medical coaxial cable comprising:
a coaxial cable main body that transmits the video signal; and the medical coaxial connectors according to claim 7 that are installed at both ends of the coaxial cable main body.

10. A medical observation system comprising:
a medical signal processing device configured to output a video signal according to examination results of a subject;
a display device configured to display an image based on the video signal; and
the medical coaxial cable according to claim 9 that connects the medical signal processing device and the display device, and that transmits the video signal from the medical signal processing device to the video signal, wherein
the medical signal processing device and the display device each include the other-side medical coaxial connector configured to be connected to the medical coaxial connector installed at one of both ends of the medical coaxial cable.

11. The medical coaxial connector according to claim 7, wherein the cylindrical portion surrounds the internal conductor along an entirety of the internal conductor in a radial direction.

12. The medical coaxial connector according to claim 7, wherein the insulating body and the cylindrical portion are spaced apart from each other in a radial direction.

13. The medical coaxial connector according to claim 7, wherein the cylindrical portion has a plurality of slits extending from the leading end to a base end.

14. A medical coaxial connector of a Bayonet Neill Concelman type adapted to be connected to an other-side medical coaxial connector, and transmit to the other-side medical coaxial connector a video signal according to examination results of a subject,
the other-side medical coaxial connector including
an other-side inner conductor, and
an other-side outer conductor electrically insulated from the other-side inner conductor and formed in a tubular shape surrounding the other-side inner conductor,
the medical coaxial connector comprising:
an internal conductor configured to be electrically connected to the other-side inner conductor when the medical coaxial connector is connected to the other-side medical coaxial connector;
an outer conductor electrically insulated from the internal conductor, formed in a tubular shape surrounding the internal conductor, and configured to be electrically connected to the other-side outer conductor when the medical coaxial connector is connected to the other-side medical coaxial connector;
an insulating body that is placed on inner periphery side of the outer conductor and formed in a cylindrical shape surrounding the internal conductor; and
a cylindrical portion provided between the outer conductor and the insulating body,
wherein the insulating body is configured to be placed on inner periphery side of the other-side outer conductor and a leading end of the insulating body in a connection direction toward the other-side coaxial connector is configured to protrude more in the connection direction than the internal conductor when the medical coaxial connector is connected to the other-side medical coaxial connector,
wherein the cylindrical portion is configured to be electrically connected to the outer conductor and inner periphery surface of the other-side outer conductor when the medical coaxial connector is connected to the other-side medical coaxial connector, and
wherein the internal conductor is configured to be inserted in the other-side inner conductor when the medical coaxial connector is connected to the other-side medical coaxial connector.

15. The medical coaxial connector according to claim 14, wherein the outer conductor is configured to position on outer periphery side of the other-side outer conductor when the medical coaxial connector is connected to the other-side medical coaxial connector.

16. A medical coaxial cable adapted to transmit a video signal according to examination results of a subject, the medical coaxial cable comprising:
a coaxial cable main body that transmits the video signal; and
the medical coaxial connectors according to claim 14 that are installed at both ends of the coaxial cable main body.

17. A medical observation system comprising:
a medical signal processing device configured to output a video signal according to examination results of a subject;
a display device configured to display an image based on the video signal; and
the medical coaxial cable according to claim 16 that connects the medical signal processing device and the display device, and that transmits the video signal from the medical signal processing device to the video signal, wherein
the medical signal processing device and the display device each include the other-side medical coaxial connector configured to be connected to the medical coaxial connector installed at one of both ends of the medical coaxial cable.

18. The medical coaxial connector according to claim 14, wherein the cylindrical portion surrounds the internal conductor along an entirety of the internal conductor in a radial direction.

19. The medical coaxial connector according to claim 14, wherein the insulating body and the cylindrical portion are spaced apart from each other in a radial direction.

20. The medical coaxial connector according to claim 14, wherein the cylindrical portion has a plurality of slits extending from the leading end to a base end.

* * * * *